US00PP35415P3

(12) United States Plant Patent
Olesen

(10) Patent No.: US PP35,415 P3
(45) Date of Patent: Oct. 10, 2023

(54) ROSE PLANT NAMED 'POULTY028'

(50) Latin Name: *Rosa hybrida*
Varietal Denomination: Poulty028

(71) Applicant: Mogens Nyegaard Olesen, Fredensborg (DK)

(72) Inventor: Mogens Nyegaard Olesen, Fredensborg (DK)

(73) Assignee: POULSER ROSER A/S, Fredensborg (DK)

( * ) Notice: Subject to any disclaimer, the term of this patent is extended or adjusted under 35 U.S.C. 154(b) by 0 days.

(21) Appl. No.: 17/803,627

(22) Filed: Sep. 13, 2022

(65) Prior Publication Data

US 2023/0189674 P1 Jun. 15, 2023

(30) Foreign Application Priority Data

Sep. 24, 2021 (QZ) ..... PBR 2021/2348

(51) Int. Cl.
*A01H 5/02* (2018.01)
*A01H 6/74* (2018.01)

(52) U.S. Cl.
USPC ..... Plt./116
CPC ..... *A01H 6/749* (2018.05)

(58) Field of Classification Search
USPC ..... Plt./116
CPC ..... A01H 6/749; A01H 5/02
See application file for complete search history.

(56) References Cited

PUBLICATIONS

Floraland Catalog (Year: 2020).*

* cited by examiner

*Primary Examiner* — Keith O. Robinson

(57) ABSTRACT

A new garden rose plant of the Miniature class which has abundant, yellow orange flowers and attractive foliage. This new and distinct variety has shown to be uniform and stable in the resulting generations from asexual propagation.

1 Drawing Sheet

Botanical designation: *Rosa hybrida.*

Variety denomination: 'Poulty028'.

This application claims priority to Plant Breeder's Rights Application Number 2021/2348, which was filed at the Community Plant Variety Rights Office in the European Union on Sep. 24, 2021, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also, an unnamed seedling. Both of the parent varieties are non-patented.

The two parents were crossed during the summer of 2015 and the resulting seeds were planted in a controlled environment in Fredensborg, Denmark. The new variety, named 'Poulty028', originated as a single seedling from the stated cross.

The new variety may be distinguished from its male pollen parent and female seed parent primarily by the following characteristics. The female seed parent plant has light yellow flowers while the new variety has yellow orange flowers. The male pollen parent plant has Yellow Group 13B flowers while the new variety has Yellow-Orange Group 21A flowers.

The objective of the hybridization of this rose variety was to create a new and distinct variety with unique qualities, such as:

1. Uniform and abundant yellow orange flowers with long lasting quality;

2. Vigorous, but compact growth when propagated on its own roots;
3. Exceptional disease resistance.

This combination of qualities is not present in previously available commercial cultivars of this type, known to the inventor, and distinguish 'Poulty028' from all other varieties of which we are aware.

As part of the rose development program, Mogens N. Olesen germinated the seeds from the aforementioned hybridization during winter of 2015 and conducted evaluations on the resulting seedlings in a controlled environment in Fredensborg, Denmark. 'Poulty028' was selected in the spring of 2016 by the inventor as a single plant from the progeny of the aforementioned hybridization.

Asexual reproduction of 'Poulty028' by rooted cuttings was first done by Mogens N. Olesen in the nursery in Fredensborg, Denmark in July, 2016. This initial and other subsequent asexual propagations conducted in controlled environments have demonstrated that the characteristics of 'Poulty028' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulty028'. Specifically illustrated in the drawing are open flowers at various stages of development, flower petals detached revealing reproductive flower parts, sepals detached showing receptacle, mature leaves, juvenile leaves, and bare stem. Plants shown are 6 months of age.

DETAILED DESCRIPTION OF THE VARIETY

The following is a description of 'Poulty028', as observed in its growth in a glass house located in Odense Denmark. Observed plants are 6 months of age, and were grown on their own roots in 24 cm containers. Color references are made using The Royal Horticultural Society (London, England) Colour Chart, 2001, except where common terms of color are used.

For a comparison, several physical characteristics of the rose variety 'Poulty015', U.S. Plant Pat. No. 26,017 are now compared to 'Poulty028'. The comparison has a general tonality of flower of Yellow Group 10C with intonations of Yellow-Orange Group 23C. The claimed plant has a general flower tonality of Yellow-Orange Group 21A. While petal count of the comparison variety is 75 petals, the claimed plant has 43 petals. Both varieties have similar growth characteristics.

FLOWER AND FLOWER BUD

Blooming habit: Continuous, and early flowering.

Flower bud:

- *Size.*—Upon opening, 20 mm in length from base of receptacle to end of bud. Bud diameter is 12 mm.
- *Bud form.*—Ovoid.
- *Bud color.*—As sepals divide petals are Yellow Group 12A and Yellow-Orange Group 23B.
- *Sepal inner surface.*—Color: Yellow-Green Group 146D and Yellow-Green Group 147B. Surface: Lightly pubescent.
- *Sepal outer surface.*—Color: Yellow-Green Group 144A and Yellow-Green Group 147A. Texture: Smooth.
- *Sepal shape.*—Apex: Cirrhose. Base: Flat at union with receptacle.
- *Sepal margin.*—Margins have strong foliaceous appendages on three of the five sepals.
- *Sepal size.*—About 26 to 36 mm long, 11 to 15 mm wide.
- *Receptacle.*—Texture: Smooth. Size: 7 mm in height, 9 mm wide. Color: Yellow-Green Group 144A. Shape: Campanulate.
- *Pedicel.*—Surface: Smooth. Length: About 32 mm. Diameter: 2.5 mm on average. Color: Yellow-Green Group 144A. Strength: Strong.
- *Peduncle.*—Length: 30 to 40 mm. Diameter: About 3 mm. Color: Yellow-Green Group 144A. Texture: Smooth.

Flower bud development: Flower buds are borne in clusters of about 3 flower buds per stem and single.

Flower bloom:

- *Fragrance.*—Moderate floral scent.
- *Duration.*—The blooms have a duration on the plant of approximately 25 days. Petals fall cleanly away from plant after flowers have fully matured.
- *Size.*—Flower diameter is 47 mm when open. Flower depth is 17 mm.
- *Flower shape.*—Rosette, double flower, with many slightly overlapping petals of different sizes.
- *Shape of flower, side view.*—The upper portion is convex. The lower portion is flat concave.

Petalage: Under normal conditions, flowers have about 43 petals.

General tonality of flower: Open flowers are Yellow-Orange Group 21A.

Petal color:

- *Upon opening, outer and inner petals.*—Upper surface: Yellow-Orange Group 23A. At basal zone Yellow Group 9A. Lower surface: Basal zone Yellow Group 13C. Middle and marginal zone Yellow-Orange Group 23A.
- *After opening, outer and inner petals.*—Upper surface: Yellow-Orange Group 16A at marginal and middle zone. Basal zone Yellow Group 6B. Lower surface: Basal zone Yellow Group 9C. Marginal and middle zone Yellow-Orange Group 15A.

Petals:

- *Petal reflex.*—Strong.
- *Margin.*—Entire and uniform. No undulations.
- *Shape.*—Broad and elliptic. Apex shape: Rounded. Base shape: Acute.
- *Size.*—25 mm (l) 26 mm (w).
- *Texture.*—Smooth.
- *Thickness.*—Average.

Petaloids:

- *Size.*—13 mm (l) by 5 mm (w).
- *Quantity.*—About 8.
- *Shape.*—Elliptical with an acute base and rounded apices. Strong undulations.
- *Color.*—The upper and lower sides are Yellow-Orange Group 23A.

Reproductive flower parts:

- *Pollen.*—None observed.
- *Anthers.*—Size: 1.5 mm in length. Color: Yellow Group 10D. Quantity: 32 on average.
- *Filaments.*—Color: Yellow Group 7A. Length: 6 mm.
- *Pistils.*—Length: 10 mm. Quantity: 20 on average.
- *Stigmas.*—Color: Green-Yellow Group 1C.
- *Styles.*—Color: Green-Yellow Group 1D.
- *Location of stigmas.*—Superior in location relative to the length of the filaments and the height of the anthers.
- *Hips.*—None Observed.

Plant

Plant growth: Upright. Plants are 50 cm in height, and 40 cm wide.

Stems:

- *Color of juvenile growth.*—Yellow-Green Group 144B.
- *Color of mature growth.*—Yellow-Green Group 146B.
- *Length.*—Canes are about 27 cm from the base of the plant to the flowering portion.
- *Diameter.*—About 3.5 mm.
- *Internodes.*—On mature canes about 31 mm between nodes.
- *Surface texture.*—Young wood: Smooth. Older wood: Smooth.

Long prickles: None observed.

Plant foliage:

- *Compound leaf.*—90 mm (l)×65 (w).
- *Quantity.*—3 leaves per 10 cm of stem on average.
- *Leaf bearing angle to the stem.*—45 degrees.

*Color of juvenile foliage*.—Upper side: Yellow-Green Group 144A. Lower side: Yellow-Green Group 144B shaded with intonations of Greyed-Orange Group 172A.

*Color of mature foliage*.—Upper side: Yellow-Green Group 147A. Lower side: Yellow-Green Group 148B.

Plant leaves and leaflets:

*Stipules*.—Size: 6 mm long, 2 mm wide. Quantity: 2 per compound leaf. Shape: Linear, slightly broad based with outward extending apices. Margins: Finely serrated. Color: Yellow-Green Group 144A.

*Petiole*.—Length: 10 mm. Diameter: 2 mm. Upper surface color: Yellow-Green Group 144A. Lower surface color: Yellow-Green Group 144A.

*Rachis*.—Length: 30 mm. Upper surface color: Yellow-Green Group 144A with some intonations of Greyed-Purple Group 183A. Lower surface color: Yellow-Green Group 144A.

*Leaflet*.—Quantity: Normally 5 to 7 leaflets. Margins: Serrated. Size: Terminal leaflets are about 46 mm long, 25 mm wide. Shape: Generally elliptical. Base: Rounded. Apex: Acute. Texture: Smooth. Thickness: Average. Arrangement: Odd pinnate. Venation: Reticulate. Glossiness: Moderately glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant named 'Poulty028' substantially as described and illustrated herein.

* * * * *

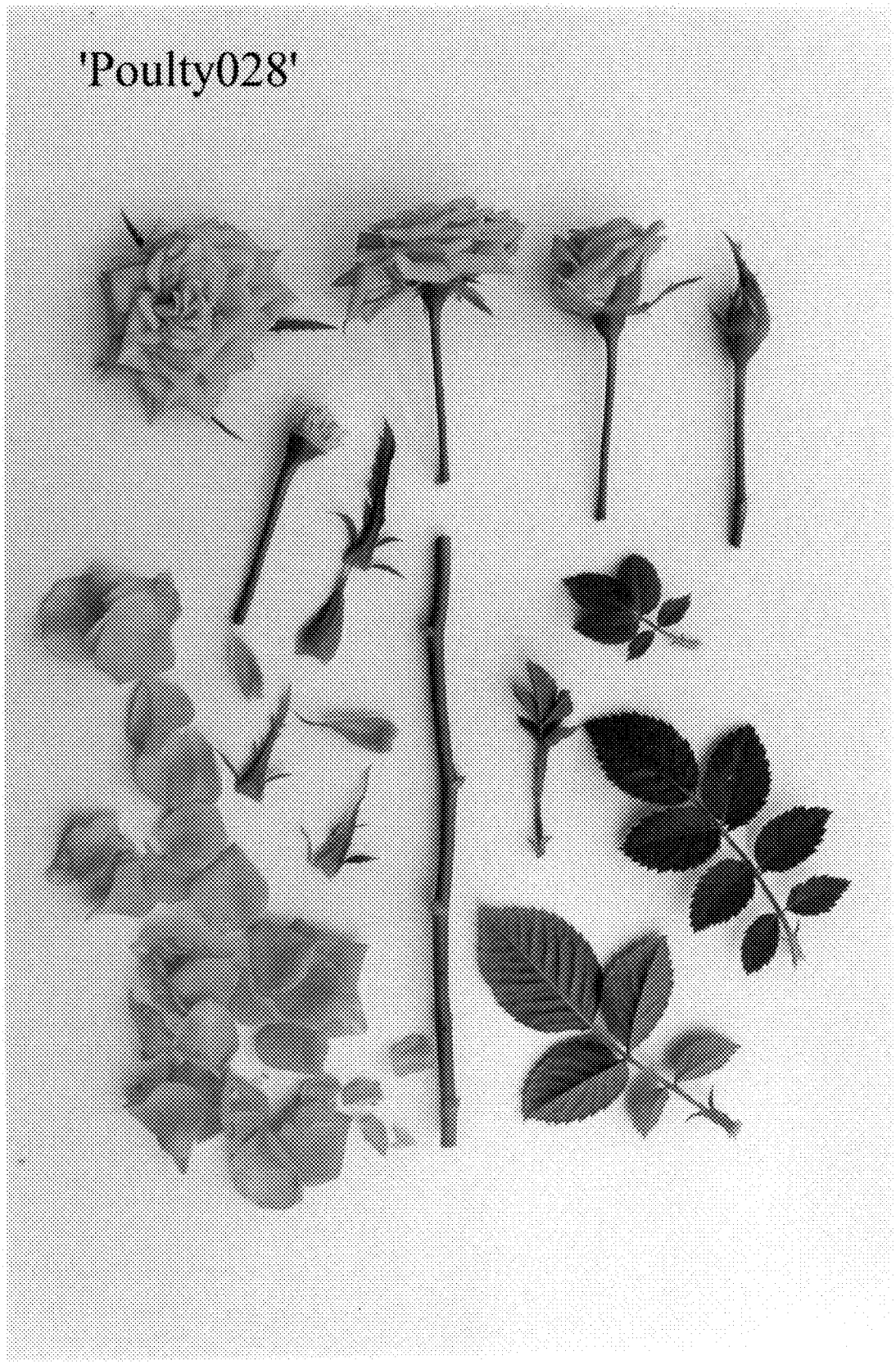
'Poulty028'